United States Patent
Heuer

(10) Patent No.: US 10,595,903 B2
(45) Date of Patent: Mar. 24, 2020

(54) OSTEOSYNTHESIS DEVICE

(71) Applicant: SILONY MEDICAL INTERNATIONAL AG, Frauenfeld (CH)

(72) Inventor: Frank Heuer, Filderstadt (DE)

(73) Assignee: SILONY MEDICAL INTERNATIONAL AG, Frauenfeld (CH)

( * ) Notice: Subject to any disclaimer, the term of this patent is extended or adjusted under 35 U.S.C. 154(b) by 105 days.

(21) Appl. No.: 15/747,984

(22) PCT Filed: Jun. 3, 2016

(86) PCT No.: PCT/EP2016/062595
§ 371 (c)(1),
(2) Date: Jan. 26, 2018

(87) PCT Pub. No.: WO2017/016717
PCT Pub. Date: Feb. 2, 2017

(65) Prior Publication Data
US 2018/0214183 A1    Aug. 2, 2018

(30) Foreign Application Priority Data
Jul. 29, 2015  (DE) .................. 10 2015 214 384

(51) Int. Cl.
*A61B 17/70*  (2006.01)
*A61B 17/86*  (2006.01)

(52) U.S. Cl.
CPC ...... *A61B 17/7032* (2013.01); *A61B 17/7037* (2013.01); *A61B 17/7038* (2013.01); *A61B 17/7098* (2013.01); *A61B 17/864* (2013.01)

(58) Field of Classification Search
CPC ............ A61B 17/7032; A61B 17/7034; A61B 17/7035; A61B 17/7037
See application file for complete search history.

(56) References Cited

U.S. PATENT DOCUMENTS

2009/0036934 A1  2/2009  Biedermann et al.
2010/0114180 A1  5/2010  Rock et al.

FOREIGN PATENT DOCUMENTS

EP    0836835 A2    4/1998
EP    2301458 A1    3/2011
(Continued)

OTHER PUBLICATIONS

International Serach Report and Written Opinion Form PCT/ISA/210 and PCT/ISA/237, International Application No. PCT/EP2016/062595, pp. 1-7, International Filing Date Jun. 3, 2016, mailing date of search report dated Sep. 13, 2016.

*Primary Examiner* — Ellen C Hammond
(74) *Attorney, Agent, or Firm* — Bond Schoeneck & King, PLLC; George McGuire

(57) ABSTRACT

Osteosynthesis device, in particular a pedicle screw, having a bone anchor, in particular a bone screw, with a shank and a head, and having a fork head which is U-shaped in a side view and which has two arms at a proximal end area and is formed in one piece, wherein the head of the bone anchor is mounted pivotably on a distal end area of the fork head directed away from the arms, wherein the fork head has, at the distal end area, a receiving opening for the head of the bone anchor, which receiving opening is delimited in the radial direction by spring portions, wherein the spring portions are delimited radially inwards by the receiving opening and radially outwards by an annular groove arranged concentrically with respect to the receiving opening, said annular groove forming a seat for a securing element, wherein the head of the bone anchor is inserted into the receiving opening from the direction of the distal end of the fork head.

9 Claims, 6 Drawing Sheets

(56) References Cited

FOREIGN PATENT DOCUMENTS

| | | | |
|---|---|---|---|
| EP | 2570090 | B1 | 4/2015 |
| FR | 2794637 | A1 | 12/2000 |
| WO | 0072770 | A1 | 12/2000 |

OSTEOSYNTHESIS DEVICE

CROSS-REFERENCE TO RELATED APPLICATIONS

This application is the United States National Phase Entry of PCT Application No. PCT/EP2016/062595, filed Jun. 3, 2016, which claims priority to German Application No. 10-2015-214384.8 (DE), filed Jul. 29, 2015, the entire disclosure of each of which is incorporated herein by reference.

BACKGROUND OF THE INVENTION

The invention relates to an osteosynthesis device, in particular a pedicle screw.

Osteosynthesis devices of this type are well known from the prior art. Osteosynthesis devices relate in particular to the field of spinal surgery, in order to align adjacent vertebral bodies and fix said bodies in a desired position relative to one another. In the process, a bone anchor is inserted into each adjacent vertebral body, specifically is typically screwed into said body in the form of a bone screw, and these adjacent bone anchors are then connected by a correction element, typically by a correction rod, which is clamped in the fork head of a relevant osteosynthesis device in a particular position desired by a surgeon. In this way, adjacent vertebral bodies are aligned and fixed relative to one another in a desired position.

An osteosynthesis device of this type is known from EP 2 301 458 A1, for example. In this bone screw known from the prior art, the bone anchor or bone screw is inserted through a receiving opening from the proximal end area of the fork head, such that the head is mounted so as to pivot in a tapered area of the receiving opening. In order to fix the bone screw in a particular angular position determined by the surgeon, a thrust piece is provided that is inserted into the fork head from the proximal end. When fitting the bone screw, this thrust piece is moved towards the distal end area of the fork head by the correction element or correction rod by screwing a set screw into a thread of the fork head, such that said thrust piece fixes the head of the bone anchor or bone screw in the appropriate angular position relative to the fork head. In order to loosen this fixation in an angular position, it is sufficient to loosen the set screw such that the axial pressure that the correction element or correction rod exerts on the thrust piece can be taken away from the thrust piece such that the thrust piece no longer clamps the head of the bone anchor.

However, a drawback of osteosynthesis devices of this type is that the shank diameters of the bone anchors or bone screws that comprise an external thread for screwing into a bone or vertebral body are limited. It is thus not possible to insert a bone anchor or bone screw that has a shank diameter that is greater than the diameter of the head into the receiving opening from the proximal end of the fork head. Therefore, for applications that require a large shank diameter, osteosynthesis devices of this type cannot be used.

The prior art also discloses osteosynthesis devices in which a head of a bone anchor or bone screw is inserted into the fork head of the osteosynthesis device from a distal end. An osteosynthesis device of this type is known from EP 2 570 090 B1 and US 2009/0036934 A1. In this osteosynthesis device, the fork head is formed in two pieces, said head comprising a first proximal part having the arms for receiving the correction rod and comprising a distal clamping part for receiving the head of the bone screw, the outer surface of which clamping part is conical. The distal part is rotatably connected to the proximal part by means of two pins. The distal clamping part comprises resilient spring elements that delimit a receiving opening for the head of the bone screw. The head of the bone screw is inserted into the distal clamping part from the distal end, a clamping ring arranged radially outside the distal clamping part being provided for securing the head. When a surgeon is fitting this osteosynthesis device, a correction rod is again inserted between the arms of the proximal part and is moved by a set screw towards the distal end. This correction rod in turn contacts the clamping ring such that it presses the conical outer surface of the clamping part downwards such that the head of the bone screw is fixed in a particular angular position.

However, a drawback of an osteosynthesis device of this type is that it is not possible, or is only possible with difficulty, for a surgeon to correct the angular adjustment once the set screw has been tightened for the first time, since the clamping ring is already clamped on the conical outer surface of the clamping part. Loosening the set screw thus does not directly cause the angular position of the bone screw relative to the fork head to be loosened. This proves to be problematic in particular in bone screws that have already been screwed into bones or vertebral bodies. Furthermore, the multiple-part design of the fork head is complicated to fit and expensive to manufacture.

SUMMARY OF THE INVENTION

The problem addressed by the invention is therefore to provide an osteosynthesis device using which large shank diameters of the bone anchors can be implemented simply and cost-effectively, it being intended to be ensured that the angular position of the bone anchor is corrected in a simple manner.

This problem is solved by an osteosynthesis device characterized in that the spring portions are delimited radially outwards by an annular groove arranged concentrically with respect to the receiving opening, said annular groove forming a seat for a securing element.

Preferably, the spring portions are radially outwardly resilient such that the receiving opening is temporarily radially widened in order to insert the head of the bone anchor. If a securing element is not inserted into the annular groove, the spring portions can be moved from a blocking position into an insertion position. In this case, it is particularly preferable for the spring portions to be elastically deformable, such that after deforming they can be moved back into the blocking position. Advantageously, the connection between the spring portions of the fork head and the head of the bone anchor is designed as a bending snap-in connection and/or an annular snap-in connection.

According to the invention, a securing element is provided that is arranged in the annular groove such that it cannot be lost.

According to the invention, it is also provided that the annular groove is cylindrical. A cylindrical annular groove proves to be particularly advantageous because radial displacement of the spring portions can be largely or approximately largely prevented by axially introducing or inserting a securing element into the annular groove, such that by inserting the securing element the spring portions can only be prevented from being displaced into the insertion position, the head of the bone anchor being prevented from being clamped by arranging the securing element in the annular groove.

According to the invention, it is furthermore provided that the securing element is designed as a circular-ring-like, preferably cylindrical, blocking sleeve and is fastened in the annular groove. For this purpose, the blocking sleeve preferably has a cross section that is identical or almost identical to the diameter of the annular groove. In this case, the blocking sleeve advantageously corresponds to the cylindrical annular groove such that the spring portions are secured in the blocking position and cannot be moved into the release position when the blocking sleeve is fastened in the annular groove, it being possible to prevent the blocking sleeve from falling out of the annular groove at the same time, and the head of the bone anchor not being clamped, or practically not being clamped, by the spring portions or the blocking sleeve. It is therefore particularly preferable for the head of the bone anchor to be clamped only by a thrust piece that is inserted into the fork head from the proximal end, and is compressed in the fork head and is moved axially against the head of the bone anchor when fitting a correction element or correction rod such that it is fixed in the relevant angular deflection thereof.

Advantageously, the blocking sleeve is fastened by press-fitting, clamping, bonding, riveting, welding or screwing. It is also conceivable for the annular groove and/or the blocking sleeve to have at least one conical surface designed to make it easier to fasten the blocking sleeve in the annular groove such that it cannot be lost.

Another advantageous embodiment of the osteosynthesis device provides that the receiving opening is delimited radially outwards by a circular-ring portion that forms the spring portions. Advantageously, the circular-ring portion is then arranged between the receiving opening and the annular groove.

In this case, it is particularly advantageous for the circular-ring portion to comprise cut-outs arranged over the circumference thereof that divide the circular-ring portion into the spring portions. Advantageously, the spring portions are connected to the fork head in one piece at the proximal end and have a free end at the distal end. Preferably, a plurality of, more preferably 4 to 8, more preferably 6, cut-outs are provided.

In a preferred development of the osteosynthesis device, it is provided that the cut-outs extend in parallel with a central axis of the receiving opening. In this case, it is conceivable for the cut-outs to be cylindrical.

In another particularly advantageous development of the osteosynthesis device, it is provided that the receiving opening has an opening diameter and that the shank of the bone anchor has an external diameter, the opening diameter of the receiving opening being smaller than the largest external diameter of the shank. Using an osteosynthesis device of this type, a bone anchor comprising a shaft having a large external diameter can therefore be produced, it also being possible for the bone anchor to be securely fastened into brittle bones or vertebral bodies, for example.

It has also proven to be particularly advantageous for the head of the bone anchor to be spherical and for the spring portions to comprise retaining projections that protrude radially relative to and towards the receiving opening. Advantageously, the retaining projections are designed such that they prevent the head from falling out of the bone anchor in the axial direction.

In this case, it is particularly advantageous for the retaining projections to comprise a sliding portion designed such that the head of the bone anchor is pivotable. Advantageously, the retaining projections have a concavely spherical surface facing the distal end that is designed such that the head is mounted so as to pivot in the fork head and is also prevented from falling out of the fork head.

It is also particularly preferable for the spring portions to comprise, in the distal end area, a lead-in chamfer radially facing the receiving opening. A lead-in chamfer of this type can make it easier to push in or press in the head of the bone anchor when fitting the osteosynthesis device.

Furthermore, it is advantageous for the spring portions to have different lengths in the axial direction. Advantageously, the spring portions are asymmetrical such that greater deflection can be achieved in a first deflection direction than in a second deflection direction that is different from the first deflection direction.

BRIEF DESCRIPTION OF THE DRAWINGS

Further details and advantageous developments are found in the following description, with reference to which the embodiment shown in the drawings is described and explained in greater detail.

In the drawings.

DETAILED DESCRIPTION

Figure 1:
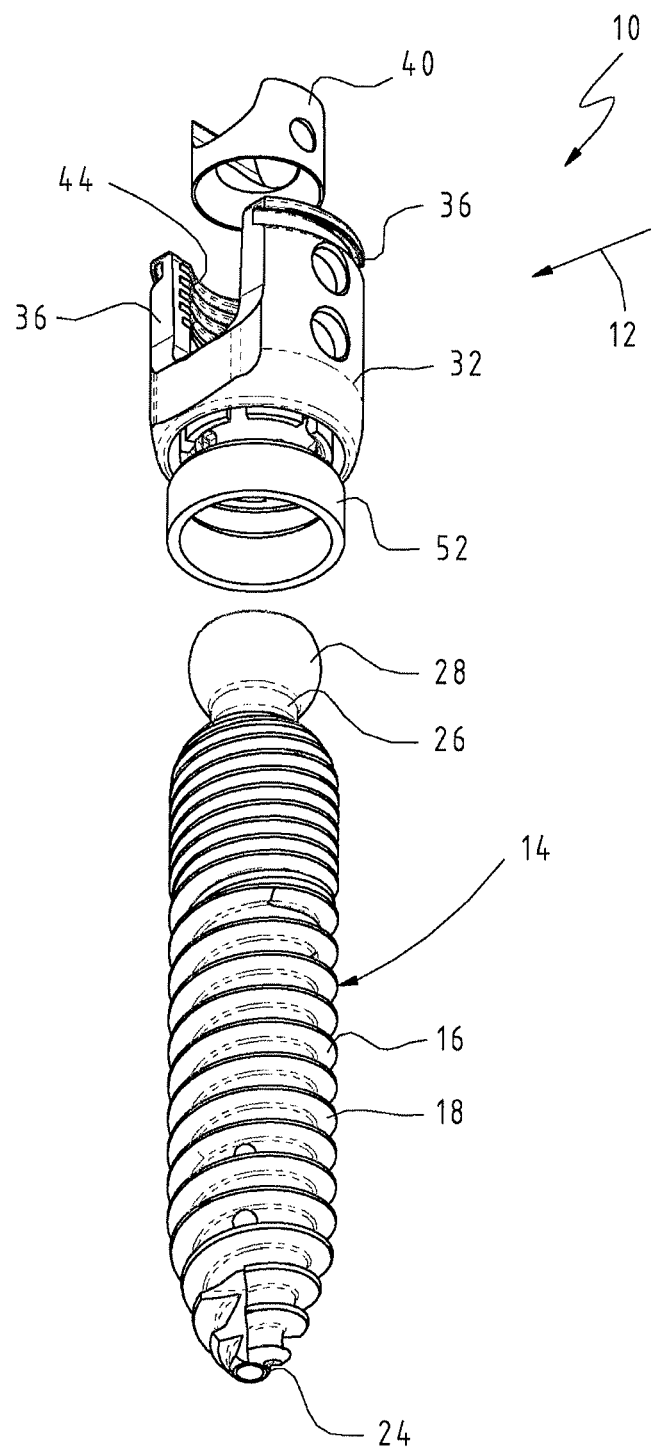
FIG. 1 is an exploded oblique view from below of an osteosynthesis device according to the invention.
Figure 2:
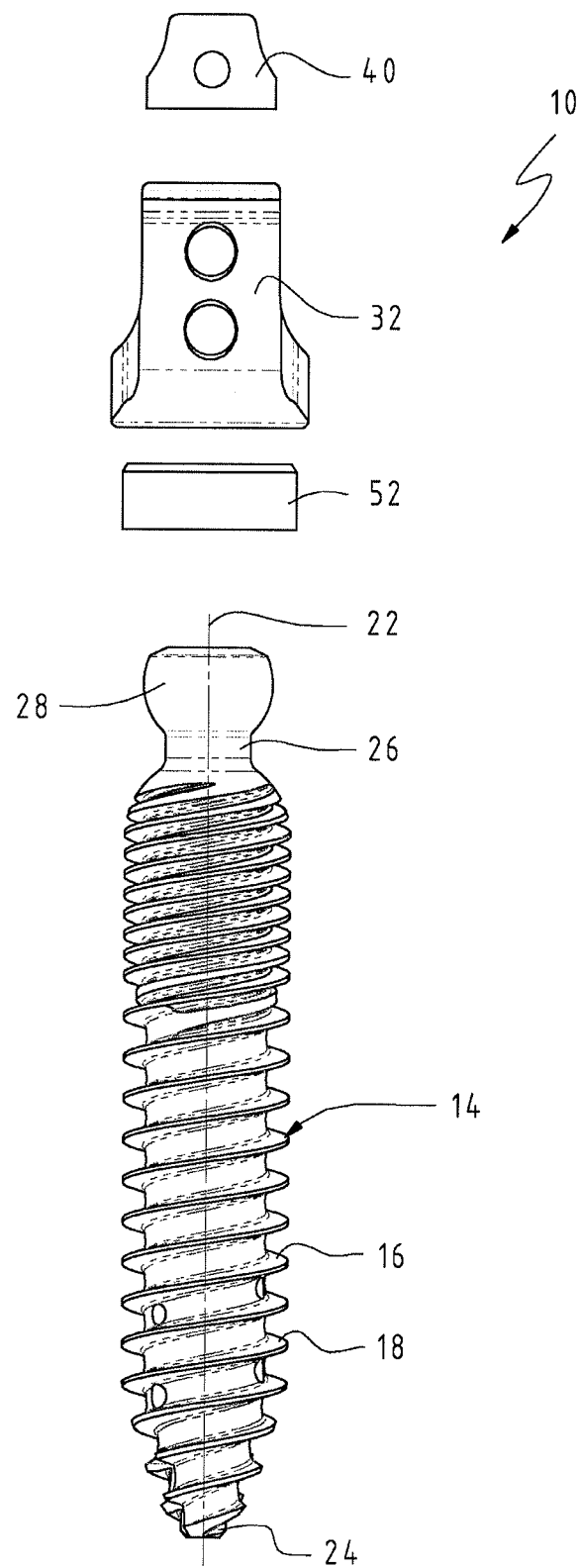
FIG. 2 is an exploded side view of the osteosynthesis device according to FIG. 1.
Figure 3:
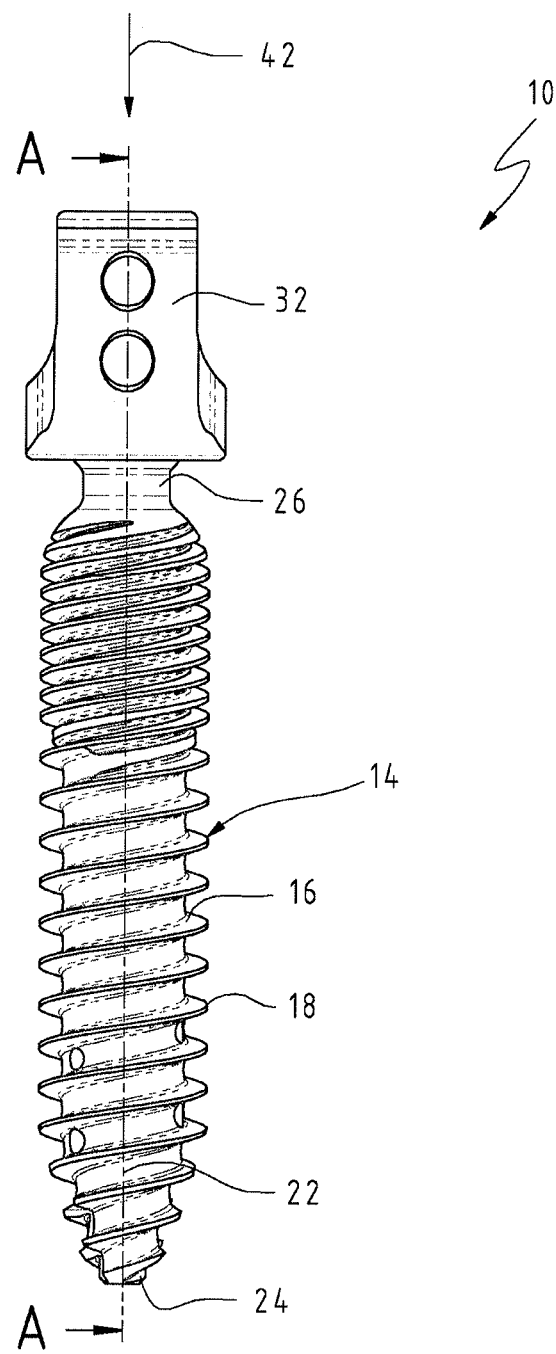
FIG. 3 is a non-exploded side view of the osteosynthesis device according to FIG. 2.
Figure 4:
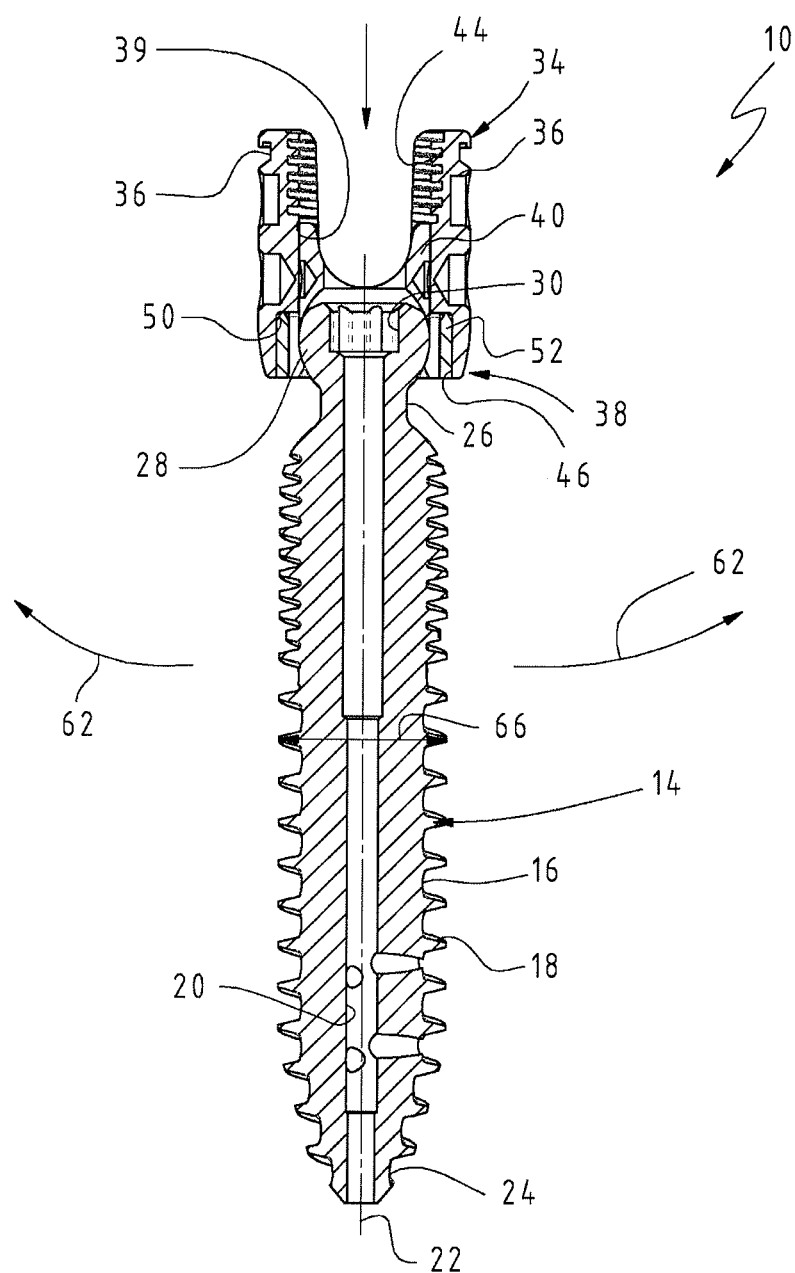
FIG. 4 shows a section through the osteosynthesis device along the line A-A according to FIG. 3.

FIGS. 1 to 4 show an osteosynthesis device 10 according to the invention that is denoted as a whole by reference sign 10 and is designed as a pedicle screw, in particular as a polyaxial screw. Corresponding components and elements in the drawings are denoted by corresponding reference signs herein. FIG. 1 is an oblique view from below of the osteosynthesis device 10. FIG. 2 is an exploded side view of the osteosynthesis device 10 when viewed in the direction of the arrow 12 in FIG. 1. FIG. 3 is a non-exploded side view of the osteosynthesis device 10 according to FIG. 2 and FIG. 4 shows a section through the osteosynthesis device 10 along the line A-A according to FIG. 3.

The osteosynthesis device 10 comprises a bone anchor 14, designed as a bone screw, which comprises a shank 16 having an external thread 18. The bone anchor 14 or the shank 16 thereof is cannulated, i.e. it has a continuous longitudinal hole 20 that is concentric with a central longitudinal axis 22 of the bone anchor 14 or the shank 16. The bone anchor 14 may also comprise transverse holes (not shown in the drawings) that are connected to the longitudinal hole 20. By means of the longitudinal hole 20 and the transverse holes, bone cement can be applied between the shank 16 and a patient's bone. The shank 16 comprises a drilling tip 24 at one end, by means of which the bone anchor 14 can be screwed into a bone. At the end remote from the drilling tip 24, the bone anchor 14 comprises a neck 26 designed as a narrowed portion, to which a head 28 of the bone anchor 14 is connected in the direction of the central longitudinal axis 22. In the head 28, the bone anchor 14 further comprises a torque transmission portion 30 in the form of a hexagon profile or a torx profile which is concentric with the central longitudinal axis 22 and by means of which the bone anchor 14 can be driven in rotation, such that it can be screwed into a patient's bone.

The osteosynthesis device 10 also comprises a fork head 32 formed in one piece. The fork head 32 receives the bone anchor 14, and, in a side view shown in the section according to FIG. 4, the fork head 32 is U-shaped and comprises two arms 36 in a proximal end area 34. The head 28 of the bone anchor 14 is mounted on a distal end area 38 of the fork head 32 remote from the arms 36 so as to pivot in the manner of a spherical bearing, and can be fixed in various positions to be set by a surgeon relative to the fork head 32.

For this purpose, in the interior 39 of the fork head 32, the osteosynthesis device 10 comprises a movably compressed thrust piece 40, which is axially movable in a defined area. In order to specify pivoting of the bone anchor 14, from the proximal end area 34 of the fork head 32, a clamping force is exerted on the thrust piece 40 in the direction of an arrow 42 by means of clamping elements (not shown), such as a set screw and a correction rod (likewise not shown) arranged between the arms 36 in the fork head 32, and therefore the thrust piece 40 is in turn pressed onto the head 28 of the bone anchor 14.

In order to receive a clamping element designed as a set screw, for example, the fork head 32 comprises an internal thread 44 in the interior 39 in the proximal end area 34. Before tightening the clamping element, a correction rod, which is known per se, is inserted between the head 28 of the bone anchor 14 and the clamping element, it being possible to fix the entire assembly in position by tightening the clamping element, which typically only takes place once the bone anchor 14 is inserted into the patient's bone in its intended position. After inserting the bone anchor 14, the fork head 32 and the correction rod inserted into the interior 39 of the fork head 32 are oriented relative to the bone anchor 14 and are fixed in the position intended by the surgeon by tightening the clamping element.

In the distal end area 38, the fork head 32 comprises a receiving opening 46 for the head 28 of the bone anchor 14, the head 28 of the bone anchor 14 being inserted into the receiving opening 46 from the distal end of the fork head 32.

Figure 5:
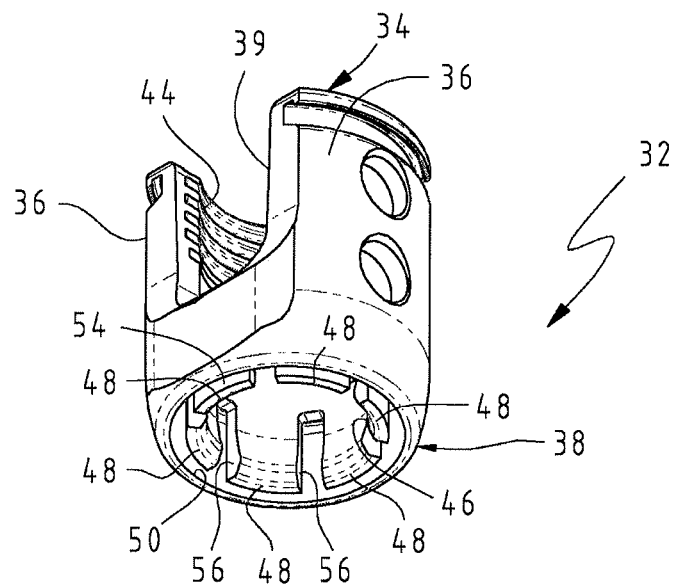
FIG. 5 is an oblique view of a fork head of the osteosynthesis device according to FIGS. 1 to 4.
Figure 6:
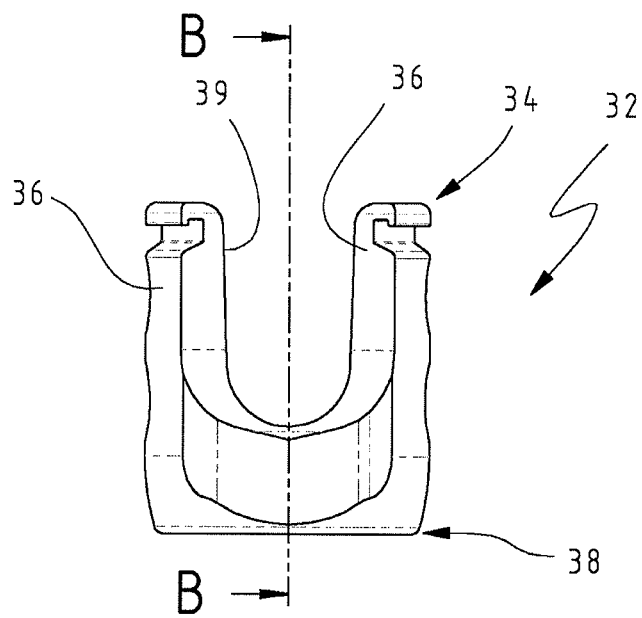
FIG. 6 is a side view of the fork head according to FIG. 5.
Figure 7:
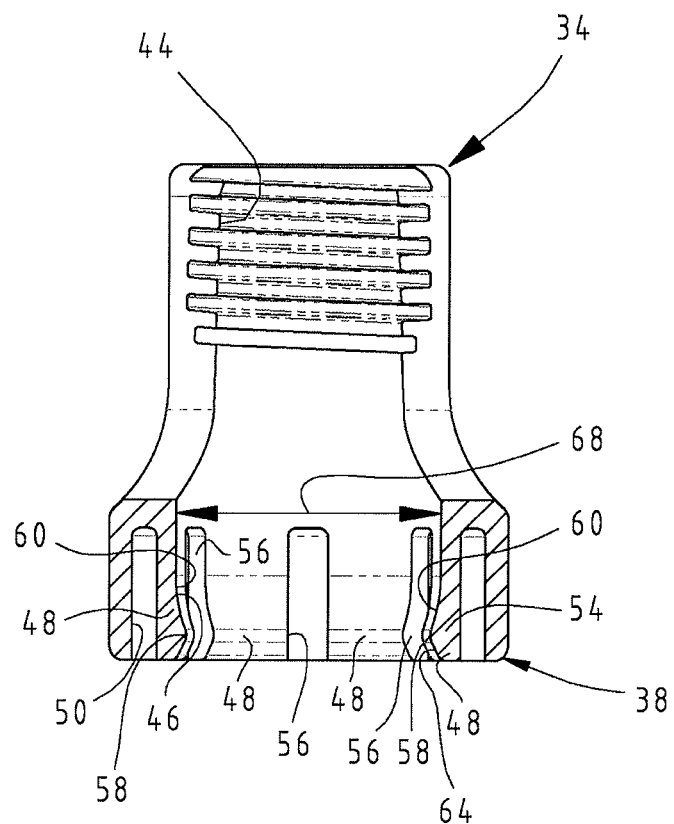
FIG. 7 shows a section through the fork head along the line B-B according to FIG. 6.

The fork head 32 is shown by itself in FIGS. 5 to 7, with the mode of operation of the osteosynthesis device 10 according to the invention being described and explained in greater detail with reference to FIGS. 4 to 7. In its distal end area, the fork head 32 comprises the receiving opening 46 for the head 28 of the bone anchor 14. The receiving opening 46 is delimited by resilient spring portions 48 in the radial direction, which portions are in turn radially outwardly delimited by a cylindrical annular groove 50 arranged concentrically with the receiving opening 46.

A securing element 52 that is designed as a circular-ring-like, cylindrical blocking sleeve and can be clearly seen in FIGS. 1, 2 and 4 is pressed into the annular groove 50. The securing element 52 corresponds to the annular groove 50 such that, although it is arranged in the annular groove 50 such that it cannot be lost, no or almost no radial clamping force is exerted on the spring portions 48. In another embodiment, which is not shown in the drawings, the securing element 52 may also be designed as an oval blocking sleeve, it also being possible for the groove to be oval, such that the blocking sleeve can be prevented from rotating in the oval groove.

The receiving opening 46 is delimited radially outwards by a circular-ring portion 54 that forms the spring portions 48. For this purpose, the circular-ring portion 54 comprises cut-outs 56 arranged over the circumference thereof that extend in parallel with a central axis of the receiving opening 46 and divide the circular-ring portion 54 into the spring portions 48.

Furthermore, the head 28 of the bone anchor 14 is spherical, the spring portions 48 comprising retaining projections 58 that protrude radially relative to the receiving opening 46 and prevent the head 28 of the bone anchor 14 from falling out of the receiving opening 46. The retaining projections 58 comprise a sliding portion 60 designed such that the head 28 of the bone anchor 14 is pivotable in the direction of the double arrow 62. The sliding portion 60 is concavely spherical, such that the spherical head 28 of the bone anchor 14 can slide thereon. The spring portions 48 comprise, in the distal end area 38, a lead-in chamfer 64 radially facing the receiving opening 46.

The shank 16 of the bone anchor 14 has an external diameter 66 on the external thread 16, the receiving opening 46 having an opening diameter 68. At its largest dimensions, the external diameter 66 of the shank 16 is greater than the internal diameter of the receiving opening 46, and therefore the bone anchor 14 cannot be inserted through the receiving opening 46 from above, i.e. from the proximal end area 34.

The osteosynthesis device 10 is fitted as follows:

The bone anchor 14 is pushed or pressed into the receiving opening 46 in the fork head 32 from the distal end area 34 of the fork head 32 such that the resilient spring portions 48 are moved radially outwards into an insertion position and yield into the annular groove 50. At this point, the securing element 52 is not yet fitted in the annular groove 50. After pushing or pressing the head 28 of the bone anchor 14, the spring portions are resiliently moved back into the blocking position shown in FIG. 4, the retaining projections 58 axially undercutting the head 28 of the bone anchor 14 such that bone anchor 14 is prevented from falling out of the receiving opening 46.

After pushing or pressing the head 28 of the bone anchor 14 into the receiving opening 46, the spring portions 48 are secured in the blocking position by arranging the securing element 52 in the annular groove 50. Here, the securing element 52, which is arranged in the annular groove 50 such that it cannot be lost by being pressed in, for example, merely prevents the spring portions 48 from being able to be moved radially outwards into the release position. According to the invention, it is not desirable for radial clamping force to be exerted on the head 28 of the bone anchor 14 by the spring portions 48.

In order to specify axial pivoting of the bone anchor 14 relative to the fork head 32, as described at the outset, from the proximal end area 34, a clamping force is exerted on the thrust piece 40 by means of clamping elements (not shown) or a correction rod (not shown), which piece in turn secures the head 28 of the bone anchor in its relevant position as determined by a surgeon.

In order to achieve asymmetrical deflection of the bone anchor 14, it may also be provided that the spring portions 48 are designed to be asymmetrical, for example, such that greater deflection can be achieved in one direction than in the opposite direction.

What is claimed is:

1. An osteosynthesis device comprising, a bone anchor with a shank and a head, and a fork head which is U-shaped in a side view and which has two arms at a proximal end area and is formed in one piece, wherein the head of the bone anchor is mounted pivotably on a distal end area of the fork head remote from the arms, wherein the fork head has, at the distal end area, a receiving opening for the head of the bone anchor, which receiving opening is delimited in the radial direction by spring portions, wherein the spring portions are delimited radially inwards by the receiving opening, wherein the head of the bone anchor is inserted into the receiving opening from the direction of the distal end of the fork head, wherein the spring portions are delimited radially outwards by an annular groove arranged concentrically with respect to the receiving opening, said annular groove forming a seat for a securing element, wherein the annular groove is cylindrical, wherein a securing element is provided that is arranged in the annular groove such that it cannot be lost, and wherein the securing element is designed as a circular-ring-like blocking sleeve and is fastened in the annular groove.

2. The osteosynthesis device according to claim 1, wherein the receiving opening is delimited radially outwards by a circular-ring portion that forms the spring portions.

3. The osteosynthesis device according to claim 2, wherein the circular-ring portion comprises cut-outs arranged over the circumference thereof that divide the circular-ring portion into the spring portions.

4. The osteosynthesis device according to claim 3, wherein the cut-outs extend in parallel with a central axis of the receiving opening.

5. The osteosynthesis device according to claim 1, wherein the receiving opening has an opening diameter and in that the shank of the bone anchor has an external diameter, the opening diameter of the receiving opening being smaller than the largest external diameter of the shank.

6. The osteosynthesis device according to claim 1, wherein the head of the bone anchor is spherical and in that the spring portions comprise retaining projections that protrude radially relative to and towards the receiving opening.

7. The osteosynthesis device according to claim 6, wherein the retaining projections comprise a sliding portion designed such that the head of the bone anchor is pivotable.

8. The osteosynthesis device according to claim 1, wherein the spring portions comprise, in the distal end area, a lead-in chamfer radially facing the receiving opening.

9. The osteosynthesis device according to claim 1, wherein the spring portions have different lengths in the axial direction.

* * * * *